United States Patent [19]
Unno et al.

[11] Patent Number: 6,056,980
[45] Date of Patent: May 2, 2000

[54] PROCESS FOR PRODUCING STARCH SUGAR COMPOSITION

[75] Inventors: Takehiro Unno, Fuji; Teruo Nakakuki, Mishima; Takeshi Yamamoto, Fuji; Yutaka Konishi; Tadao Hirose, both of Tokyo, all of Japan

[73] Assignees: Nihon Shokuhin Kako Co., Ltd.; Kirin Beer Kabushiki Kaisya, both of Tokyo; Takeda Food Products Ltd., Osaka, all of Japan

[21] Appl. No.: 09/011,189

[22] PCT Filed: May 15, 1997

[86] PCT No.: PCT/JP97/01642

§ 371 Date: Jan. 14, 1998

§ 102(e) Date: Jan. 14, 1998

[87] PCT Pub. No.: WO97/43435

PCT Pub. Date: Nov. 20, 1997

[30] Foreign Application Priority Data

May 15, 1996 [JP] Japan ................................... 8-145171
May 15, 1996 [JP] Japan ................................... 8-145172

[51] Int. Cl.$^7$ ........................................................ A23L 1/09
[52] U.S. Cl. ............................. 426/48; 536/126; 426/661
[58] Field of Search .................................... 426/548, 658, 426/661, 48; 536/102, 123.1, 123.13, 123, 124, 126

[56] References Cited

U.S. PATENT DOCUMENTS 5,436,329  7/1995  Caboche ................................. 536/103

FOREIGN PATENT DOCUMENTS 3022958  1/1991  Japan .
7059559  3/1995  Japan .

OTHER PUBLICATIONS

"Preparation and Properties of Immobilized Buckwheat α–Glucosidase" by Ken–ichi Kanaya, Motoki Sasaki, Koji Kawashima, Seiya Chiba and Tokuji Shimomura (Nippon Nógeikagaku Kaishi, vol. 53, No. 12, pp. 385–390 (1979)).

"Enzymatic Syntheses of Glucobioses by a Condensation Reaction with α–Glucosidase, β–Glucosidases and Glucoamylase" by Hiroshi Fujimoto, Hiroko Nishida and Katsumi Ajisaka (Agric. Biol. Chem., 52 (6), 1345–1351, (1998)).

"Development of Cyclodextrin and Its Application" by Shoichi Kobayashi, et al., Food Industries, vol. 31, No. 4, Feb. 29, 1998.

"Seibutsu Kagaku Jikkensho 25, Denpun–Kanren Kouso Jikkensho (Biochemical Experimental Methods, 25, Experimental Methods on Starch and Related Sugar Enzymes)" Gakkai Shuppan Center, (1989).

*Primary Examiner*—Keith D. Hendricks
*Attorney, Agent, or Firm*—Smith, Gambrell & Russell, LLP

[57] ABSTRACT

At least one enzyme selected from α-amylase of various types, an oligosaccharide-forming amylase, β-amylase and a debranching enzyme and an enzyme capable of forming nigerooligosaccharide by transglycosylation and/or condensation reaction are allowed to successively or simultaneously act on a material comprised of at least one selected from i) starch, ii) a maltooligosaccharide with a degree of polymerization not lower than maltose and iii) a dextrin, to form nigerooligosaccharide, which is thereafter optionally reduced to obtain a starch sugar composition containing the nigerooligosaccharide or a reduction product thereof. This starch sugar composition may be added to food and drink as at least part of its sweeteners, whereby various advantages can be provided, e.g., not only a sweetness can be imparted, but also the quality of sweetness can be improved, and the moisture retention of foods can be improved.

7 Claims, No Drawings

PROCESS FOR PRODUCING STARCH SUGAR COMPOSITION

This application is a 371 of PCT/JP97/01642, filed May 15, 1997.

TECHNICAL FIELD

This invention relates to a process for producing a starch sugar composition containing nigerooligosaccharide or a reduction product thereof, a starch sugar composition containing nigerooligosaccharide alcohols, and food and drink containing such a starch sugar composition.

BACKGROUND ART

In recent years, food life has become rich in variety. With regard to sweeteners added to foods, too, it has become required to satisfy various factors such as low sweetness, refreshing sweetness, low viscosity, water retention and heat resistance. Of these, as for the low sweetness, an attempt to achieve it by, e.g., merely adding sugar to food and drink in a smaller quantity results in a low-bodied taste, and hence relatively high-molecular weight starch sugars such as dextrin of various types have been used in order to lower the sweetness while keeping a saccharide concentration. In addition thereto, in recent years, various oligosaccharides have been put into use.

However, as stated above, what is needed for sweeteners is not merely a low sweetness but also various factors such as a well-bodied taste, a flavorfullness and harmony with other seasoning materials, and hence the sweeteners can not meet all these requirements. Thus, it is sought to further provide a new sweetener.

As one of the above oligosaccharides, nigerooligosaccharide has began to attract notice. As a process for producing this nigerooligosaccharide, the following process is known in the art.

For example, M. Stacey and J. M. Webber, Methods in Carbohydrate Chemistry, I, pp.339–341, Academic press 1962, discloses a proposal on a process in which nigeran, erucinan or the like, which is a polysaccharide produced by microorganisms, is used as a substrate and hydrolysis is carried out using an enzyme or an acid to produce the nigerooligosaccharide.

A process is also known in which the transglycosylation and/or condensation reaction of known α-glucosidase is utilized to produce nigerose (see Ken-ichi Kaneda et al., The Society of Japan Agricultural Chemistry, 53, pp.385–390, 1979; H. Fujimoto et al., Agric. Biol. Chem., 52, pp.1345–1351, 1988; etc.)

Japanese Patent Application Laid-open No. 3-22958 also discloses a process in which a cyclodextrin glucanotransferase is allowed to act on a starch hydrolyzate to produce nigerose.

Japanese Patent Application Laid-open No. 7-59559 still also discloses a process in which at least one of glycosyltransferases that provide α-1,3-linkage is allowed to act on a substrate containing an α-1,4-glucoside-linked polysaccharide or oligosaccharide, to produce the nigerooligosaccharide.

However, the process disclosed in M. Stacey and J. M. Webber, Methods in Carbohydrate Chemistry, I, pp.339–341, Academic press 1962, requires nigeran, erucinan or the like, which is so much expensive that it is not preferable as a process for enabling industrial and inexpensive mass production.

The process making use of α-glucosidase can only produce the nigerooligosaccharide in a very small quantity.

The process disclosed in Japanese Patent Application Laid-open No. 3-22958 requires the cyclodextrin glucanotransferase in a quantity 50 times or more than usual, and also is known to produce the nigerooligosaccharide in a small quantity (see Shoichi Kobayashi et al., Food Industries, 31, pp.20–29, 1988).

The process disclosed in Japanese Patent Application Laid-open No. 7-59559 can only produce the nigerooligosaccharide in an amount of 26.1% by weight per saccharide solid content, as so disclosed in Examples described in the publication, which is not a sufficient yield.

Thus, none of the conventional processes have achieved the mass production of nigerooligosaccharide in an industrial scale and inexpensively, and have been sought to be further improved so that the products can be used as sweeteners of food and drink.

Various dextrins and various oligosaccharides which are used partly in place of sugar in order to achieve a low sweetness while keeping a well-bodied taste have been unsatisfactory in view of quality of sweetness and physical properties such as heat resistance, acid resistance, moisture retention and low coloring properties and also in respect of the requirement for lower calorie.

The present invention was made taking account of the above problems. Accordingly, an object of the present invention is to provide a process for producing a starch sugar composition, which can mass-produce nigerooligosaccharide or its reduction products in an industrial scale and inexpensively; a starch sugar composition having the quality of a low sweetness and good sweetness and superior physical properties; and food and drink containing such a starch sugar composition.

DISCLOSURE OF THE INVENTION

To achieve the above object, the first of the present invention provides a process for producing a starch sugar composition, comprising the step of allowing an enzyme capable of forming nigerooligosaccharide by transglycosylation and/or condensation reaction, to act on a substrate comprised of an aqueous saccharide solution containing a saccharide with a degree of glucose polymerization of 2 or more in an amount of at least 50% by weight in saccharide solid content to form nigerooligosaccharide in an amount of at least 30% by weight in the saccharide solid content.

The second of the present invention provides, in the first embodiment of the present invention, a process for producing a starch sugar composition, wherein the aqueous saccharide solution containing a saccharide with a degree of glucose polymerization of 2 or more in an amount of at least 50% by weight in saccharide solid content comprises an aqueous saccharide solution obtained by allowing at least one selected from an α-amylase, a β-amylase, an oligosaccharide-forming amylase and a debranching enzyme to act on a starch-liquefying solution.

The third of the present invention provides a process for producing a starch sugar composition, comprising the step of allowing at least one selected from an α-amylase, a β-amylase, an oligosaccharide-forming amylase and a debranching enzyme and an enzyme capable of forming nigerooligosaccharide by transglycosylation and/or condensation reaction, to simultaneously act on a starch-liquefying solution to form nigerooligosaccharide in an amount of at least 30% by weight in the saccharide solid content.

The fourth of the present invention provides a process for producing a starch sugar composition, comprising the step of allowing at least one enzyme selected from α-amylase of various types, an oligosaccharide-forming amylase, a β-amylase and a debranching enzyme and an enzyme capable of forming nigerooligosaccharide by transglycosylation and/or condensation reaction, to successively or simultaneously act on a material comprised of at least one selected from i) starch, ii) a maltooligosaccharide with a degree of polymerization not lower than maltose and iii) a dextrin to form nigerooligosaccharide, followed by reduction.

The fifth of the present invention provides a starch sugar composition comprising a plurality of nigerooligosaccharide alcohols.

The sixth of the present invention provides food and drink comprising a plurality of nigerooligosaccharide alcohols.

The seventh of the present invention provides, in the sixth embodiment of the present invention, food and drink comprising the nigerooligosaccharide alcohols and a sweetener other than the nigerooligosaccharide alcohols.

The eighth of the present invention provides, in the sixth embodiment of the present invention, food and drink comprising the nigerooligosaccharide alcohols and the sweetener other than the nigerooligosaccharide alcohols, wherein the sweetener other than the nigerooligosaccharide alcohols is at least one selected from sucrose, starch syrup, starch powder, glucose, fructose, maltose, isomerized saccharide, lactose, honey, coupling sugar, fructosyloligosaccharide, erythritol, sorbitol, maltitol, xylitol, mannitol, lactitol, reduced xylooligosaccharide, reduced glucose syrup, Aspartame, alitame, saccharin, glycyrrhizin, stevioside, rebaudioside and sucuralose.

According to the first of the present invention, an aqueous saccharide solution containing a saccharide with a degree of glucose polymerization of 2 or more in an amount of at least 50% by weight in saccharide solid content is used as a substrate, and an enzyme capable of forming nigerooligosaccharide by transglycosylation and/or condensation reaction is allowed to act on it. Thus, a starch sugar composition can be obtained which contains the nigerooligosaccharide in an amount of as large as 30% by weight or more in the saccharide solid content.

According to the second of the present invention, at least one selected from an α-amylase, a β-amylase, an oligosaccharide-forming amylase and a debranching enzyme is allowed to act on a starch-liquefying solution to prepare the aqueous saccharide solution containing a saccharide with a degree of glucose polymerization of 2 or more in an amount of at least 50% by weight in saccharide solid content. Thus, a starch sugar composition containing the nigerooligosaccharide can be obtained at a low cost.

According to the third of the present invention, at least one selected from an α-amylase, a β-amylase, an oligosaccharide-forming amylase and a debranching enzyme and an enzyme capable of forming nigerooligosaccharide by transglycosylation and/or condensation reaction are allowed to simultaneously act on a starch-liquefying solution. Thus, a starch sugar composition can be obtained which contains the nigerooligosaccharide in an amount of as large as 30% by weight or more in the saccharide solid content.

According to the fourth of the present invention, at least one enzyme selected from α-amylase of various types, an oligosaccharide-forming amylase, β-amylase and a debranching enzyme and an enzyme capable of forming nigerooligosaccharide by transglycosylation and/or condensation reaction are allowed to successively or simultaneously act on a material comprised of at least one selected from i) starch, ii) a maltooligosaccharide with a degree of polymerization not lower than maltose and iii) a dextrin, whereby a sugar composition having nigerooligosaccharide in a high content can be obtained. This sugar composition may be reduced, whereby a starch sugar composition containing nigerooligosaccharide alcohols can be produced in an industrial scale, with ease and in large quantities.

According to the fifth of the present invention, the composition contains nigerooligosaccharide alcohols obtained by reduction of the nigerooligosaccharide. Thus, a starch sugar composition can be provided which is low sweet and has a very refined sweetness, has a low calorie, a low cariosity, a body-providing effect, a moisture retention effect, a lustering effect and film-forming properties, and has a superior stability to heat, acid and alkali. Incidentally, the nigerooligosaccharide alcohols have a much more refreshing sweetness than the nigerooligosaccharide, and are saccharides hardly digestible and having a low calorie. When they are added to food and drink, they can more improve the heat resistance, low coloring properties and moisture retention of food and drink than the nigerooligosaccharide.

According to the sixth of the present invention, the food and drink contain the starch sugar composition containing the nigerooligosaccharide alcohols. Thus, food and drink can be provided which have been endowed with the superior properties inherent in the nigerooligosaccharide.

According to the seventh and eighth of the present invention, the food and drink contains the nigerooligosaccharide alcohols and the other sweeteners. Thus, food and drink can be provided, having an excellent flavor because of the nigerooligosaccharide alcohols and the other sweeteners the both of which are well balanced without damaging the excellent properties of the nigerooligosaccharide alcohol and rather cooperatively act to exhibit an effect.

BEST MODES FOR WORKING THE INVENTION

In the present invention, the nigerooligosaccharide refers to an oligosaccharide with a degree of glucose polymerization of 2 or more, containing at least one α-1,3 -glucosidic linkage, such as nigerose, nigerosylglucose and nigerosylmaltose. It may preferably be an oligosaccharide with a degree of glucose polymerization of from 2 to 10, and more preferably be an oligosaccharide with a degree of glucose polymerization of from 2 to 7, and may include not only oligosaccharides comprised of only α-1,3-glucosidic linkages but also oligosaccharides comprised of α-1,3-glucosidic linkages and other glucosidic linkages. The nigerooligosaccharide alcohol refers to a saccharide alcohol obtained by reducing the nigerooligosaccharide.

In the present invention, as the substrate, it is preferable to use an aqueous saccharide solution containing a saccharide with a degree of glucose polymerization of 2 or more in an amount of at least 50% by weight in saccharide solid content. If the saccharide with a degree of glucose polymerization of 2 or more is in an amount less than 50% by weight in saccharide solid content, it is difficult to make the content of nigerooligosaccharide not less than 30% by weight in the saccharide solid content of the resultant nigerooligosaccharide-containing syrup. There are no particular limitations on the concentration of the aqueous saccharide solution. It may preferably be from 1 to 75% by weight, and more preferably from 10 to 35% by weight.

The saccharide with a degree of glucose polymerization of 2 or more may preferably be a maltooligosaccharide with a degree of glucose polymerization of from 2 to 10, such as maltose, maltotriose and maltotetraose, and a dextrin with a degree of glucose polymerization of 11 or more. It may more preferably be chiefly composed of maltooligosaccharide, and may more preferably be chiefly composed of maltose-maltopentaose.

The aqueous saccharide solution containing the saccharide with a degree of glucose polymerization of 2 or more in an amount of at least 50% by weight in saccharide solid content may be prepared by any methods. Preferably, it may be prepared by allowing at least one selected from α-amylase, β-amylase, an oligosaccharide-forming amylase and a debranching enzyme to act on a starch-liquefying solution. Stated specifically, e.g., an aqueous saccharide solution chiefly composed of maltose can be obtained by allowing β-amylase (EC 3.2.1.2) and a debranching enzyme to act on a starch-liquefying solution so prepared as to have a glucose equivalent weight of from 0.5 to 20. In this method, the β-amylase may be replaced with an oligosaccharide-forming amylase to obtain an aqueous saccharide solution chiefly composed of maltooligosaccharide having a degree of glucose polymerization corresponding to the type of the oligosaccharide-forming amylase. The starch-liquefying solution, after it has been decomposed with α-amylase, may be further subjected to conventional separation and removal of chromatographic fractions to obtain an aqueous saccharide solution containing the saccharide with a degree of glucose polymerization of 2 or more in an amount of at least 50% by weight in saccharide solid content.

As starch powder serving as a material for the starch-liquefying solution, any powders may be used, e.g., potato starch powder, cane sugar powder, corn starch powder, waxy corn starch powder, cassava starch powder. As the α-amylase, β-amylase, oligosaccharide-forming amylase and debranching enzyme, any of those known in the art may be used.

In the present invention, the enzyme that forms the nigerooligosaccharide by transglycosylation and/or condensation reaction may be any of enzymes capable of forming α-1,3-glucosidic linkages by transglycosylation and/or condensation reaction. For example, it is preferable to use, e.g., nigerooligosaccharide glucanotransferase produced by a strain belonging to the genus Acremonium, as disclosed in Japanese Patent Application Laid-open No. 7-59559. For example, as the strain belonging to the genus Acremonium, Acremonium sp. S4G13 strain may preferably be employed (name of deposition agency: National Institute of Bioscience and Human Technology Agency of Industrial Science and Technology, Ministry of International Trade and Industry; address of deposition agency: 1-3, Higashi 1-chome, Tsukuba-shi, Ibaraki-ken, Japan; date of deposition: Aug. 2, 1993; deposition number: FERM BP-4373: depositor: Kirin Brewery Co., Ltd.; address of depositor: 26-1, Jingumae 6-chome, Shibuya-ku, Tokyo, Japan). The nigerooligosaccharide glucanotransferase can be obtained by, e.g., culturing the above strain under aerobic conditions to make the nigerooligosaccharide glucanotransferase accumulate in a culture medium, followed by its collection.

Conditions under which the enzyme capable of forming nigerooligosaccharide by transglycosylation and/or condensation reaction is allowed to react on the substrate may preferably be conditions adapted to the respective enzymes. For example, when the nigerooligosaccharide glucanotransferase produced by the strain belonging to the genus Acremonium is allowed to act on the substrate, it is preferable to add the nigerooligosaccharide forming enzyme to the substrate in an amount of from 0.01 to 5 units/g substrate and allow the former to act on the latter under conditions of pH 4 to 10 and 30 to 70° C.

To measure the enzymatic activity of the nigerooligosaccharide glucanotransferase, 0.25 ml of an enzyme solution is added in 0.75 ml of a maltose solution prepared by dissolving maltose in a 20 mM phosphate buffer (pH 7.0) in a concentration of 0.66% by weight, to carry out reaction at 37° C., where the amount of enzyme for forming 1 μmol of glucose in one minute from the substrate maltose is defined to be one unit.

In the process for producing a starch sugar composition according to the present invention, the enzyme capable of forming nigerooligosaccharide by transglycosylation and/or condensation reaction is allowed to act on the substrate comprised of the aqueous saccharide solution containing the saccharide with a degree of glucose polymerization of 2 or more in an amount of at least 50% by weight in saccharide solid content; the solution being prepared by, e.g., allowing at least one selected from an α-amylase, β-amylase, an oligosaccharide-forming amylase and a debranching enzyme to act on the starch-liquefying solution. The enzyme of at least one selected from an α-amylase, a β-amylase, an oligosaccharide-forming amylase and a debranching enzyme and the enzyme capable of forming nigerooligosaccharide by transglycosylation and/or condensation reaction may be allowed to simultaneously act on the starch-liquefying solution. In this instance, the reaction of saccharification attributable to the enzyme of at least one selected from α-amylase, β-amylase, an oligosaccharide-forming amylase and a debranching enzyme proceeds in parallel to the reaction of the nigerooligosaccharide glucanotransferase, so that the substrate saccharide with a degree of glucose polymerization of 2 or more is sufficiently supplied. Hence, a nigerooligosaccharide-containing syrup can be obtained which contains the nigerooligosaccharide in an amount of at least 30% by weight in saccharide solid content. When the enzyme of at least one selected from an α-amylase, a β-amylase, an oligosaccharide-forming amylase and a debranching enzyme and the enzyme capable of forming nigerooligosaccharide by transglycosylation and/or condensation reaction are allowed to simultaneously act on the starch-liquefying solution, the reaction may preferably be carried out under conditions falling in agreement with reaction and/or conditions for the respective enzymes.

The starch sugar composition thus obtained, containing the nigerooligosaccharide in an amount of at least 30% by weight in saccharide solid content, may be used as syrup as it is, or may be optionally further purified so that the content of nigerooligosaccharide can be made higher. It may be purified by, e.g., a method in which an organic solvent such as an alcohol is added to the syrup to effect precipitation fractionation of oligosaccharides; a method in which saccharides other than the nigerooligosaccharide are removed by chromatography making use of carbon-celite columns, chromatography employing a method of making separation in accordance with molecular weights by gel permeation, or chromatography making use of ion-exchange resin; or a method in which yeast is added to the syrup to utilize fermentable saccharides.

The starch sugar composition containing nigerooligosaccharide may be reduced to obtain a starch sugar composition containing a nigerooligosaccharide alcohol. It can be reduced under reaction and/or conditions for reducing usual sugar alcohols. For example, the reduction reaction may preferably be carried out in the presence of a reducing catalyst having a high reaction selectivity such as Raney nickel catalyst, at a saccharide solution concentration of from 20 to 75% by weight, at a temperature of from 80 to 150° C., at a hydrogen pressure of from 10 to 250 kg/cm$^2$ and for a reaction time of from 30 to 240 minutes. As the catalyst, besides the Raney nickel catalyst, various metal catalysts may be used, which, however, may require maintenance of the reducing catalyst because hydrolysis of saccharides may progress with a decrease in activity as the reduction reaction proceeds. The catalyst may be used in an amount, which may vary depending on the reduction activity of catalysts, of from 1 to 5% by weight based on the weight of saccharide solid content in the case of commercially available Raney nickel catalysts. By this reduction reaction, the starch sugar composition containing nigerooligosaccharide alcohol can be obtained.

The starch sugar composition thus obtained, containing nigerooligosaccharide or its reduction product, may be optionally purified by, e.g., decoloring and deodorizing it using activated carbon, deionizing it using ion-exchange resins and controlling its content by chromatography or the like. It may be optionally further treated, e.g., may be concentrated, may be powdered by spray drying or granulation drying or may be molded to provide products with various forms such as liquids, powders, granules, molded products or mixtures with other components.

The starch sugar composition containing the nigerooligosaccharide in an amount of at least 30% by weight in saccharide solid content, obtained according to the first to third of the present invention, has superior properties, e.g., it is low sweet and has a refined sweetness, can be appropriately colored by heating and has a superior moisture retention. Thus, it may be added to various food and drink to impart various advantages to them.

The starch sugar composition containing the nigerooligosaccharide alcohols, obtained by the fourth of the present invention, is low sweet and has a very refined sweetness, has a low calorie, a low cariosity, a body-providing effect, a moisture retention effect, a lustering effect and film-forming properties, and has a superior stability to heat, acid and alkali, because of the nigerooligosaccharide alcohols contained. Thus, it may be added to various food and drink to impart such various advantages to them. The starch sugar composition obtained in the present invention may be applied to not only food and drink but also feed, cosmetics of various types, pharmaceuticals and so forth.

The starch sugar composition obtained in the present invention may also be added to food and drink in combination with other sweetening components. For example, it may be used in combination with at least one selected from saccharides such as sucrose, starch syrup, starch powder, glucose, fructose, maltose, isomerized saccharide, lactose, honey, coupling sugar and fructosyloligosaccharide, sugar alcohols such as erythritol, sorbitol, maltitol, xylitol, mannitol, lactitol, reduced xylooligosaccharide and reduced glucose syrup, and high-sweeteness sweeteners such as Aspartame, alitame, saccharin, glycyrrhizin, stevioside, rebaudioside and sucuralose. If necessary, it may also be used in the form of a mixture with extenders such as dextrin and starch.

The starch sugar composition obtained in the present invention, taking note of the low cariosity that is one of its properties, may be used in confectionery, e.g., chewing gum, chocolate, crackers or biscuits, coockies, caramels and candies as a coating sweetener or a sweetener of the confectionery itself, may be used to sweeten, or improve the quality of sweetness of, drinks such as colas, soda pop, juice, coffee, black tea and various health drinks, or may be used to sweeten, improve the quality of sweetness of, or improve taste or feel of, toothpaste, mouthwash, gargling water, rouge and so forth.

The present starch sugar composition has not only the effect of sweetening usual food and drink, improving the taste of them or improving the quality of them, but also the effect of enhancing saltiness and other deliciousness while smoothing them without causing denaturation or reaction even in the presence of amino acids. Hence, it may also effectively used in various seasonings such as soy sauce, powdery soy sauce, miso (Japanese style bean paste), powdery miso, various food flour (sprinkled over boiled rice), mayonnaise, dressing, vinegar, soy and vinegar, powdery sushi vinegar, noodle soup, sauce, catchup, tare (dip sauce) for roast meat, curry roux, stew material, stock material, various composite seasonings, sweet sake for seasoning, fresh sweet sake for seasoning, tabletop sugar, coffee sugar, Chinese food material and tempura (fried food) dip soup.

In addition, the present starch sugar composition is low sweet and has a very refined sweetness, and hence it has not only the effect of sweetening but also the effect of improving the quality of taste such as body-providing and also has a lustering effect and a protein denaturation preventive effect. Hence, it may be used in various food and drink such as rice crackers, rice-cake cubes, millet-and-rice cakes, rice cakes, bean-jam buns, Turkish delight, bean paste and jam, sweet beans jelly, jelly, castella (sponge cake), candy, bread, pies or tarts, crackers, biscuits, pudding, waffles, butter cream, custard cream, cream puffs, sponge cake, doughnuts, ice cream and sherbet, pastes such as flour paste, peanut paste and fruit paste, jams such as jam and marmalade, pickles such as fukujinzuke (sliced vegetables pickled in soy sauce), senmaizuke (sliced radishes pickled in sweetened vinegar) and rakkyouzuke (scallions pickled in sweetened vinegar), ham, sausage, marine paste products such as kamaboko (boiled fish paste) and chikuwa (boiled fish paste with a cylindrical form), ground fish meat of these materials, various delicacies, and tsukudani (food boiled down in soy sauce).

When the starch sugar composition obtained in the present invention is added to food and drink, it not only has the advantages as stated above but also has the effect of, e.g., preventing food and drink components from crystallization, improving storage stability, stabilizing enzymes and improving heat resistance.

The starch sugar composition obtained in the present invention can be added to the above food and drink in any step of their manufacturing process and by a method appropriately selected from known methods as exemplified by mixing, kneading, dissolution, melting, immersion, permeation, sprinkling, coating, spraying, injection, crystallization, hardening and granulation.

EXAMPLE 1

According to the method disclosed in Japanese Patent Application Laid-open No.7-59559, Acremonium sp. S4G13 strain (Acremonium sp. S4G13, FERM BP-4373) was aerobically cultured, and nigerooligosaccharide glucanotransferase was collected from the resultant culture medium. Using as a substrate a maltose solution with a solid content of 30% by weight, the nigerooligosaccharide glucanotransferase was added in an amount of 1 unit/g substrate, and reaction was carried out under conditions of pH 7 and 55° C. to obtain nigerooligosaccharide-containing syrup. Saccharide composition of the nigerooligosaccharide-containing syrup thus obtained was analyzed to obtain the results as shown in Table 1.

EXAMPLE 2

Nigerooligosaccharide-containing syrup was obtained in the same manner as in Example 1 except that the substrate used therein was replaced with a solution with a solid content of 30% by weight, containing maltose and glucose in a weight ratio of 5:5 in the solid content. Saccharide composition of this nigerooligosaccharide-containing syrup was analyzed to obtain the results as shown in Table 1.

COMPARATIVE EXAMPLE 1

Nigerooligosaccharide-containing syrup was obtained in the same manner as in Example 1 except that the substrate used therein was replaced with a solution with a solid content of 30% by weight, containing maltose and glucose in a weight ratio of 3:7 in the solid content. Saccharide composition of this nigerooligosaccharide-containing syrup was analyzed to obtain the results as shown in Table 1.

EXAMPLE 3

Corn starch was liquefied using α-amylase by a conventional method to obtain a starch-liquefying solution with a concentration of 30% by weight and a glucose equivaqlent of 7.

Subsequently, this starch-liquefying solution was adjusted to have pH 5. Thereafter, based on 1 part by weight of starch used as a material, 0.001 part by weight of β-amylase (trade name: "β-amylase 1500", available from Nagase Biochemicals, Ltd.) and 0.0001 part by weight of isoamylase (available from Hayashibara Biochemical Laboratories, Inc.) were added thereto, and reaction was carried out at 55° C. for 24 hours to obtain a substrate.

Thereafter, to the substrate thus obtained, the nigerooligosaccharide glucanotransferase produced by the genus Acremonium strain, prepared by the method disclosed in Japanese Patent Application Laid-open No.7-59559, was added in an amount of 0.8 unit/g substrate, and reaction was carried out at 55° C. for 48 hours to obtain nigerooligosaccharide-containing syrup. Saccharide composition of this nigerooligosaccharide-containing syrup was analyzed to obtain the results as shown in Table 1.

EXAMPLE 4

Corn starch was treated in the same manner as in Example 3 to obtain a starch-liquefying solution.

Subsequently, this starch-liquefying solution was adjusted to have pH 5. Thereafter, the same β-amylase and isoamylase as those used in Example 3, used in the same quantities as in Example 3, and the same nigerooligosaccharide glucanotransferase as the above used in an amount of 1.2 unit/g substrate were simultaneously added, and reaction was carried out at 55° C. for 72 hours to obtain nigerooligosaccharide-containing syrup. Saccharide composition of this nigerooligosaccharide-containing syrup was analyzed to obtain the results as shown in Table 1.

TABLE 1

|  | Example | | Comp. Example | Example | |
|---|---|---|---|---|---|
|  | 1 | 2 | 1 | 3 | 4 |
| Glucose: | 26.5 | 52.4 | 73.3 | 25.6 | 32.5 |
| Maltose: | 12.5 | 13.1 | 7.1 | 22.9 | 12.0 |
| Nigerose: | 13.1 | 16.3 | 8.9 | 5.6 | 11.8 |
| Trisaccharide: | 19.3 | 10.8 | 6.3 | 23.1 | 15.0 |
| (nigerooligosaccharide) | (19.3) | (8.7) | (3.9) | (16.2) | (10.2) |
| Tetrasaccharide or higher saccharide: | 28.6 | 7.4 | 4.4 | 22.8 | 28.7 |
| (nigerooligosaccharide) | (28.6) | (5.1) | (1.5) | (11.2) | (8.2) |
| Total of nigerooligosaccharides: | 61.0 | 30.1 | 14.3 | 33.0 | 30.2 |

(In the table, the numerical values each indicate % by weight per saccharide solid content. Numerical values in the parentheses in the items of "Trisaccharide" and "Tetrasaccharide or higher saccharide" each indicate the amount of trisaccharide or tetrasaccharide or higher nigerooligosaccharide per saccharide solid content. Thus, the total of nigerooligosaccharides corresponds to the total of the amount of nigerose and the amount shown in the parentheses for trisaccharide and tetrasaccharide or higher saccharide.).

As can be seen from the results shown in Table 1, the syrups of Examples 1 to 4, obtained using the starch-liquefying solution containing the saccharide with a degree of glucose polymerization of 2 or more in an amount of at least 50% by weight in saccharide solid content and by allowing the nigerooligosaccharide glucanotransferase produced by the genus Acremonium strain to act on it contains the nigerooligosaccharide in an amount of at least 30% by weight in saccharide solid content. On the other hand, the syrup of Comparative Example, obtained using a starch-liquefying solution containing the saccharide with a degree of glucose polymerization of 2 or more in an amount of only 30% by weight in saccharide solid content contains the nigerooligosaccharide in an amount of as small as 14.3% by weight in saccharide solid content.

EXAMPLE 5

Potato starch was liquefied using α-amylase by a conventional method to obtain a starch-liquefying solution with a concentration of 25% by weight and a glucose equivaqlent of 5.

Subsequently, this starch-liquefying solution was adjusted to have pH 6. Thereafter, 4 units/g substrate of maltotetraose glucanotransferase (available from Nihon Shokuhin Kako Co., Ltd.) derived from Pseudomonas and 1 unit/g substrate of pullulanase (trade name: "Pullulanase Amono 3", available from Amano Pharmaceutical Co., Ltd.) were added, and reaction was carried out at 55° C. for 24 hours to obtain a substrate. The titers of the maltotetraose glucanotransferase and pullulanase were measured by the method disclosed in "SEIBUTSU KAGAKU JIKKENHO 25, DENPUN.KAN-RENKOUSO JIKKENHO (Biochemical Experimental Methods 25, Experimental Methods on Starch and Related Sugar Enzymes)", compiled by Michinori Nakamura and Keiji Kainuma, Gakkai Shuppan Center, 1989.

Thereafter, to the substrate thus obtained, the nigerooligosaccharide glucanotransferase produced by the genus Acremonium strain was added in an amount of 0.8 unit/g substrate, and reaction was carried out at 55° C. for 48 hours to obtain nigerooligosaccharide-containing syrup. Saccharide composition of this nigerooligosaccharide- containing syrup was analyzed to obtain the results as shown in Table 2.

TABLE 2

|  | Example 5 |
| --- | --- |
| Glucose: | 3.6 |
| Maltose: | 4.0 |
| Nigerose: | 6.8 |
| Trisaccharide: | 16.0 |
| (nigerooligosaccharide) | (7.1) |
| Tetrasaccharide: | 20.0 |
| (nigerooligosaccharide) | (7.0) |
| Pentasaccharide or higher saccharide: | 49.6 |
| (nigerooligosaccharide) | (9.1) |
| Total of nigerooligosaccharides: | 30.0 |

(In the table, the numerical values each indicate % by weight per saccharide solid content. Numerical values in the parentheses in the items of "Trisaccharide", "Tetrasaccharide" and "Pentasaccharide or higher saccharide" each indicate the amount of trisaccharide, tetrasaccharide or pentasaccharide or higher nigerooligosaccharide per saccharide solid content. Thus, the total of nigerooligosaccharides corresponds to the total of the amount of nigerose and the amount shown in the parentheses for trisaccharide, tetrasaccharide and pentasaccharide or higher saccharide.).

As can be seen from the results shown in Table 2, the syrup containing the nigerooligosaccharide in an amount of at least 30% by weight in saccharide solid content can be obtained also when the nigerooligosaccharide glucanotransferase is allowed to act on a substrate comprised of a saccharide solution obtained by allowing the maltotetraose glucanotransferase and pullulanase to act on the starch-liquefying solution having been prepared by liquefying potato starch.

EXAMPLE 6

The nigerooligosaccharide-containing syrup obtained in Example 3 was purified using activated carbon and ion-exchange resin, and thereafter concentrated until it had a solid content of 50% by weight.

Subsequently, 25 ml of the concentrated solution obtained was fractionated using a column of 2.6 cm diameter×100 cm long packed with an ion-exchange resin "DOWEX 88" (trade name; available from Dow Chemical Co.), at 60° C. and a space velocity of 0.1 using purified water. Thus, syrup with a higher oligosaccharide content was obtained. Saccharide composition of this syrup was analyzed to obtain the results as shown in Table 3.

EXAMPLE 7

The nigerooligosaccharide-containing syrup obtained in Example 1 was diluted with water to ⅓, and thereafter 2% by weight of bread yeast "YF Yeast" (trade name; available from Asahi Chemical Industry Co., Ltd.) was added to effect fermentation at normal temperature for 2 days.

Thereafter, the resultant fermentation solution was purified using activated carbon and ion-exchange resin. Thus, syrup with a higher oligosaccharide content was obtained. Saccharide composition of this syrup was analyzed to obtain the results as shown in Table 3.

TABLE 3

|  | Example | |
| --- | --- | --- |
|  | 6 | 7 |
| Glucose: | 9.0 | 0.3 |
| Maltose: | 18.5 | 0 |
| Nigerose: | 12.6 | 66.4 |
| Trisaccharide: | 29.4 | 24.3 |
| (nigerooligosaccharide) | (21.5) | (24.3) |
| Tetrasaccharide or higher saccharide: | 30.5 | 9.0 |
| (nigerooligosaccharide) | (17.0) | (9.0) |
| Total of nigerooligosaccharides: | 51.1 | 99.7 |

(In the table, the numerical values each indicate % by weight per saccharide solid content. Numerical values in the parentheses in the items of "Trisaccharide" and "Tetrasaccharide or higher saccharide" each indicate the amount of trisaccharide or tetrasaccharide or higher nigerooligosaccharide per saccharide solid content. Thus, the total of nigerooligosaccharides corresponds to the total of the amount of nigerose and the amount shown in the parentheses for trisaccharide and tetrasaccharide or higher saccharide.).

As can be seen from the results shown in Table 3, the nigerooligosaccharide content can be made higher when the syrup obtained by the process for producing nigerooligosaccharide-containing syrup according to the present invention is purified with activated carbon and ion-exchange resin or yeast is added to effect utilization of fermentable saccharides.

EXAMPLE 8

According to the method disclosed in Japanese Patent Application Laid-open No.7-59559, Acremonium sp. S4G13 strain (Acremonium sp. S4G13, FERM BP-4373) was aerobically cultured, and nigerooligosaccharide glucanotransferase was collected from the resultant culture medium. To a maltose solution with a solid content of 30% by weight, the nigerooligosaccharide glucanotransferase was added in an amount of 1 unit/g substrate, and reaction was carried out under conditions of pH 7 and 55° C. to obtain a saccharifying solution containing nigerooligosaccharide.

Subsequently, this saccharifying solution was adjusted to have a solid content concentration of 50% by weight, which was then reduced for 90 minutes in the presence of a Raney nickel catalyst used in an amount of 4% by weight based on the weight of solid content of the saccharifying solution, under conditions of a hydrogen pressure of 50 kg/cm$^2$ and 110° C., followed by decoloring and deionization to obtain a starch sugar composition containing nigerooligosaccharide alcohols.

Saccharide composition of the starch sugar composition thus obtained was measured. Sweetness of this starch sugar composition was also measured by the sucrose equivalent stimulation method, assuming the sweetness of sucrose as 100. Results obtained are shown in Table 4.

EXAMPLE 9

Corn starch was liquefied using α-amylase by a conventional method to obtain a starch-liquefying solution with a concentration of 30% by weight and a glucose equivalent of 7.

Subsequently, this starch-liquefying solution was adjusted to have pH 5. Thereafter, based on 1 part by weight of starch used as a material, 0.001 part by weight of β-amylase (trade name: "β-amylase 1500", available from Nagase Biochemicals, Ltd.) and 0.0001 part by weight of isoamylase (available from Hayashibara Biochemical Laboratories, Inc.) were added thereto, and reaction was carried out at 55° C. for 24 hours to obtain a substrate.

Thereafter, to the substrate thus obtained, the nigerooligosaccharide glucanotransferase produced by the genus Acremonium strain was added in an amount of 0.8 unit/g substrate, and reaction was carried out at 55° C. for 48 hours to obtain a saccharifying solution containing nigerooligosaccharide.

This saccharifying solution was reduced in the same manner as in Example 8, followed by purification to obtain a starch sugar composition containing nigerooligosaccharide alcohols.

Saccharide composition of the starch sugar composition thus obtained and its sweetness were measured in the same manner as in Example 1. Results obtained are shown in Table 4.

EXAMPLE 10

A starch-liquefying solution obtained in the same manner as in Example 9 was adjusted to have pH 5. Then, the same β-amylase and isoamylase as those used in Example 9, used in the same quantities as in Example 9, and the same nigerooligosaccharide glucanotransferase as the above used in an amount of 0.8 unit/g substrate were simultaneously added, and reaction was carried out at 55° C. for 72 hours to obtain a saccharifying solution containing nigerooligosaccharide.

This saccharifying solution was reduced in the same manner as in Example 8, followed by purification to obtain a starch sugar composition containing nigerooligosaccharide alcohols.

Saccharide composition of the starch sugar composition thus obtained and its sweetness were measured in the same manner as in Example 1. Results obtained are shown in Table 4.

TABLE 4

|  | Example | | |
| --- | --- | --- | --- |
|  | 8 | 9 | 10 |
| Sorbitol: | 27.3 | 27.1 | 32.9 |
| Maltitol: | 12.4 | 22.5 | 15.5 |
| Nigeritol: | 12.7 | 5.4 | 9.8 |
| Trisaccharide: | 19.1 | 23.0 | 14.3 |
| (nigerooligosaccharide alcohol) | (19.1) | (16.0) | (8.2) |
| Tetrasaccharide or higher saccharide: | 28.5 | 22.0 | 27.5 |
| (nigerooligosaccharide alcohol) | (28.5) | (10.4) | (6.9) |
| Total of nigerooligosaccharide alcohols: | 60.3 | 31.8 | 24.9 |
| Sweetness*: | 55 | 50 | 40 |

*on the basis of that of sucrose assumed as 100

(In the table, the numerical values each indicate % by weight per saccharide solid content. Numerical values in the parentheses in the items of "Trisaccharide" and "Tetrasaccharide or higher saccharide" each indicate the amount of trisaccharide or tetrasaccharide or higher nigerooligosaccharide alcohol per saccharide solid content. Thus, the total of nigerooligosaccharide alcohols corresponds to the total of the amount of nigeritol and the amount shown in the parentheses for trisaccharide and tetrasaccharide or higher saccharide.).

As can be seen from the results shown in Table 4, the starch sugar compositions obtained in Examples 8 to 10 contain the nigerooligosaccharide alcohols in a high content of from 24.9 to 60.3% by weight and have a sweetness of about ½ of sucrose.

EXAMPLE 11

Potato starch was liquefied using α-amylase by a conventional method to obtain a starch-liquefying solution with a concentration of 25% by weight and a glucose equivalent of 5.

Subsequently, this starch-liquefying solution was adjusted to have pH 6. Thereafter, 4 units/g substrate of maltotetraose glucanotransferase (available from Nihon Shokuhin Kako Co., Ltd.) derived from Pseudomonas and 1 unit/g substrate of pullulanase (trade name: "Pullulanase Amono 3", available from Amano Pharmaceutical Co., Ltd.) were added, and reaction was carried out at 55° C. for 24 hours to obtain a substrate. The titers of the maltotetraose glucanotransferase and pullulanase were measured by the method disclosed in "SEIBUTSU KAGAKU JIKKENHO 25, DENPUN.KAN-RENKOUSO JIKKENHO (Biochemical Experimental Methods 25, Experimental Methods on Starch and Related Sugar Enzymes)", compiled by Michinori Nakamura and Keiji Kainuma, Gakkai Shuppan Center, 1989.

Thereafter, to the substrate thus obtained, the nigerooligosaccharide glucanotransferase produced by the genus Acremonium strain was added in an amount of 0.8 unit/g substrate, and reaction was carried out at 55° C. for 48 hours to obtain a saccharifying solution containing nigerooligosaccharide.

Subsequently, this saccharifying solution was adjusted to have a concentration of 50% by weight, which was then reduced for 70 hours in the presence of a Raney nickel catalyst used in an amount of 3% by weight based on the weight of solid content of the saccharifying solution, under conditions of a hydrogen pressure of 150 kg/cm$^2$ and 125° C., followed by decoloring and deionization to obtain a starch sugar composition containing nigerooligosaccharide alcohols.

Saccharide composition of the starch sugar composition thus obtained and its sweetness were measured in the same manner as in Example 8. Results obtained are shown in Table 5.

TABLE 5

|  | Example 11 |
| --- | --- |
| Sorbitol: | 4.6 |
| Maltitol: | 4.0 |
| Nigeritol: | 6.7 |
| Trisaccharide: | 15.9 |
| (nigerooligosaccharide alcohol) | (7.0) |
| Tetrasaccharide: | 19.7 |
| (nigerooligosaccharide alcohol) | (6.9) |
| Pentasaccharide or higher saccharide: | 49.1 |
| (nigerooligosaccharide alcohol) | (11.8) |
| Total of nigerooligosaccharide alcohols: | 32.4 |
| Sweetness*: | 25 |

*on the basis of that of sucrose assumed as 100

(In the table, the numerical values each indicate % by weight per saccharide solid content. Numerical values in the parentheses in the items of "Trisaccharide", "Tetrasaccharide" and "Pentasaccharide or higher saccharide" each indicate the amount of trisaccharide, tetrasaccharide or pentasaccharide or higher nigerooligosaccharide alcohol per saccharide solid content. Thus, the total of nigerooligosaccharide alcohols corresponds to the total of the amount of nigeritol and the amount shown in the parentheses for trisaccharide, tetrasaccharide and pentasaccharide or higher saccharide.).

As can be seen from the results shown in Table 5, the starch sugar composition obtained in Example 4 contains the nigerooligosaccharide alcohols in a high content of 32.4% by weight and has a sweetness of about ¼ of sucrose.

EXAMPLE 12

The saccharifying solution containing nigerooligosaccharide obtained in Example 10 was purified using activated carbon and ion-exchange resin, and thereafter concentrated until it had a solid content of 50% by weight.

Subsequently, 25 ml of the saccharide solution obtained was fractionated using a column of 2.6 cm diameter×100 cm long packed with an ion-exchange resin "DOWEX 88" (trade name; available from Dow Chemical Co.), at 60° C. and a space velocity of 0.1 using purified water. Thus, syrup with a higher oligosaccharide content was obtained.

Thereafter, this saccharifying solution rich-containing nigerooligosaccharide was reduced in the same manner as in Example 8, followed by purification to obtain a starch sugar composition containing nigerooligosaccharide alcohols.

Saccharide composition of the starch sugar composition thus obtained and its sweetness were measured in the same manner as in Example 8. Results obtained are shown in Table 6.

TABLE 6

|  | Example 12 |
| --- | --- |
| Sorbitol: | 9.5 |
| Maltitol: | 18.4 |
| Nigeritol: | 12.5 |
| Trisaccharide: | 29.3 |
| (nigerooligosaccharide alcohol) | (21.3) |
| Tetrasaccharide or higher saccharide: | 30.3 |
| (nigerooligosaccharide alcohol) | (16.7) |
| Total of nigerooligosaccharide alcohols: | 50.5 |
| Sweetness*: | 35 |

*on the basis of that of sucrose assumed as 100

(In the table, the numerical values each indicate % by weight per saccharide solid content. Numerical values in the parentheses in the items of "Trisaccharide" and "Tetrasaccharide or higher saccharide" each indicate the amount of trisaccharide or tetrasaccharide or higher nigerooligosaccharide alcohol per saccharide solid content. Thus, the total of nigerooligosaccharide alcohols corresponds to the total of the amount of nigeritol and the amount shown in the parentheses for trisaccharide and tetrasaccharide or higher saccharide.).

As can be seen from comparison between the results shown in Table 6 and the results of Example 10 as shown in Table 4, the nigerooligosaccharide alcohol content can be made higher and the sweetness can be made lower when the saccharifying solution containing nigerooligosaccharide is treated with activated carbon and ion-exchange resin to prepare a saccharifying solution with a higher nigerooligosaccharide content, followed by reduction.

EXAMPLE 13

Preparation of Coffee Drink 32.5 g of coffee beans were extracted for 10 minutes using 520 ml of boiling water, followed by filtration to obtain 487.5 ml of a coffee extract. This coffee extract was mixed with 32.5 ml of cow's milk and 65 g of granulated sugar, and the pH of the mixture obtained was adjusted to 6.5, followed by addition of water to make the mixture in a volume of 600 ml, which was then bottled. Thereafter, the bottled mixture was sterilized at 120° C. for 30 minutes by treatment in an autoclave. The mixture thus treated is herein called a basic mix of coffee drinks.

The granulated sugar of coffee drink of this basic mix was substituted with the starch sugar composition obtained in Example 9, by 20% by weight or 50% by weight in terms of solid content. The products thus obtained are herein called a 20% by weight substituted product and a 50% by weight substituted product, respectively.

The basic mix, the 20% by weight substituted product and the 50% by weight substituted product were examined on their taste and flavor by an organoleptic test made by 30 panelists. In the organoleptic test, evaluation was made on the basis of those of the basic mix which were each regarded as 0 point and according to points recorded in the range between −4 points (dislike most) and +4 points (like most), finding an average value thereof. Results obtained are shown in Table 7.

TABLE 7

|  |  | Substituted product | |
| --- | --- | --- | --- |
|  | Basic mix | 20% by weight | 50% by weight |
| Taste: | 0 | +1.3 | +0.6 |
| Flavor: | 0 | +0.8 | +0.2 |

As can be seen from the results shown in Table 7, the coffee drinks whose granulated sugar was substituted with the starch sugar composition of the present invention by 20% by weight or 50% by weight in terms of solid content are improved in both the taste and the flavor compared with those of the basic mix. Stated specifically, these were evaluated to have a refreshing low sweetness not achievable by granulated sugar, and yet be full-bodied and also improved in flavor.

EXAMPLE 14

Preparation of Sponge Cake 200 g of beaten egg, 120 g of granulated sugar, 15 g of cow's milk and 10.3 g of water were put in a bowl, and were mixed for 9 minutes to adjust the specific gravity so as to be 0.23 to 0.25. To the mixture obtained, 100 g of wheat flour having been passed through a sieve was added, followed by mixing at a low speed for 15 minutes. Molten butter was further added, followed by mixing until the resultant mixture came to have a specific gravity of from 0.48 to 0.50, which was thereafter poured into a circular mold of 18 cm diameter and then baked for 30 minutes in an oven at 160° C. in top fire and 170° C. in bottom fire to obtain a sponge cake. This is herein called a basic mix of sponge cakes.

The granulated sugar of sponge cake of this basic mix was substituted with the starch sugar composition obtained in Example 9, by 20% by weight in terms of solid content. The product thus obtained is herein called a 20% by weight substituted product.

The basic mix and the 20% by weight substituted product were examined by a moisture retention test and an organoleptic test. The moisture retention test was made using sponge cake with a size of 2.5×2.5×2.5 cm which was put in a weighing bottle and stored at a relative humidity of 75% and at 25° C. for 7 days, where the weight change was determined. The organoleptic test was made by 20 panelists on the appearance, taste, flavor and texture of samples, on the basis of those of the basic mix which were each regarded as 0 point and according to points recorded in the range between −4 points (dislike most) and +4 points (like most), finding an average value thereof. Results obtained are shown in Table 8. In Table 8, those showing minus weight changes means that the weight is lost.

TABLE 8

|  | Basic mix | Substituted product 20% by weight |
| --- | --- | --- |
| Weight change (% by weight): |  |  |
| Storage 4th day: | −10.8 | −8.8 |
| Storage 7th day: | −20.8 | −17.2 |
| Organoleptic test: |  |  |
| Appearance; | 0 | +1.2 |
| Taste: | 0 | +1.6 |
| Flavor: | 0 | +0.9 |
| Texture: | 0 | +1.4 |

As can be seen from the results shown in Table 8, the sponge cake whose granulated sugar was substituted with the starch sugar composition of the present invention by 20% by weight has a better moisture retention than the basic mix. As also can be seen from the results of the organoleptic test, the sponge cake whose granulated sugar was substituted with the starch sugar composition of the present invention by 20% by weight has appearance, taste, flavor and texture all better than the basic mix. Stated specifically, the product whose granulated sugar was substituted with the starch sugar composition was evaluated to have a lower sweetness though having the same sugar concentration as the basic mix, have a deliciousness of egg which has been enhanced and full-bodied, be rich in flavor and be finished in good appearance.

EXAMPLE 15

Preparation of Hard Candy

In a copper-clad tin pan, 120 g of granulated sugar, 100 g of a commercially available enzyme-conversion starch syrup "MC-55" (trade name; available from Nihon Shokuhin Kako Co., Ltd.) and a small quantity of water were introduced, and were boiled down with stirring. At the time the liquid temperature reached 142° C., the fire was put out to allow the liquid to cool. At the time the temperature dropped to 130° C., 0.5 g of citric acid and 0.5 g of malic acid were kneaded into the liquid, and thereafter the kneaded product was casted into a cavity made of stainless steel, followed by cooling to obtain hard candy. This is herein called a basic mix.

The enzyme starch syrup of this basic mix was totally substituted with the starch sugar composition obtained in Example 9 to prepare a sample. This is herein called a totally substituted product.

The basic mix and the totally substituted product were examined on their color, taste and flavor by an organoleptic test made by 30 panelists. In the organoleptic test, evaluation was made on the basis of those of the basic mix which were each regarded as 0 point and according to points recorded in the range between −4 points (dislike most) and +4 points (like most), finding an average value thereof. Results obtained are shown in Table 9.

TABLE 9

|  | Basic mix | Totally substituted product |
| --- | --- | --- |
| Color: | 0 | +1.4 |
| Taste: | 0 | +2.0 |
| Flavor: | 0 | +1.5 |

As can be seen from the results shown in Table 9, the product whose enzyme starch syrup was totally substituted with the starch sugar composition of the present invention has better color, taste and flavor than the basic mix. The reason why the former has a good color is that the starch sugar composition has a better heat resistance than the enzyme starch syrup and can be colored with difficulty. The totally substituted product was also evaluated to have mild taste and flavor and have been improved desirably.

EXAMPLE 16

Preparation of Boiled Fish Paste

To 500 g of dehydrated fish meat obtained from fresh Alaska pollack by a conventional method, 20 g of sugar, 20 g of sorbitol and 1.5 g of polymerized phosphate were added, followed by mixing for 5 minutes by means of a kneader. The raw fish meat paste thus obtained was immediately freeze-stored at −20° C. About one month later, it was taken out and was defrosted under conditions of 5° C. for a day. Subsequently, 1% by weight of sodium chloride was added thereto, followed by mixing with stirring for 10 minutes by means of a silent cutter. Thereafter, a plastic case was packed with the mixture obtained, which was then heated in boiling water for 30 minutes to produce boiled fish paste. This is herein called a basic mix of boiled fish paste.

The sugar of this basic mix boiled fish paste was totally substituted with the starch sugar composition obtained in Example 10 to prepare boiled fish paste.

The boiled fish paste produced by totally substituting the sugar of the basic mix with the starch sugar composition was rich in flexibility with a controlled sweetness compared with the basic mix, showed a breaking strength of about 375 g and a depression of 8.5 mm, and had a good resistance to the teeth and a good flavor.

EXAMPLE 17

Preparation of Bean Paste

To 500 g of adzuki beans, water was added by a conventional method, followed by boiling, removal of astringency, removal of harshness and then removal of water-soluble impurities to obtain about 1,000 g of adzuki coarse bean paste. To 500 g of this adzuki coarse bean paste, 300 g of sugar and 80 g of water were added, followed by boiling, and then kneading up to a solid content of 60% by weight to obtain bean paste. This is herein called a basic mix.

The sugar of this basic mix bean paste was substituted with the starch sugar composition obtained in Example 11, by 15% by weight to similarly produce bean paste. This is herein called a 15% by weight substituted product.

The basic mix and the 15% by weight substituted product were examined by an organoleptic test made by 20 panelists. In the organoleptic test, evaluation was made on their color, taste, luster and melting in mouth, on the basis of those of the basic mix which were each regarded as 0 point and according to points recorded in the range between −4 points (dislike most) and +4 points (like most), finding an average value thereof. Results obtained are shown in Table 10.

TABLE 10

|                  | Basic mix | Substituted product 15% by weight |
|------------------|-----------|-----------------------------------|
| Color:           | 0         | +1.2                              |
| Taste:           | 0         | +2.0                              |
| Luster:          | 0         | +1.4                              |
| Melting in mouth:| 0         | +1.8                              |

As can be seen from the results shown in Table 10, the product obtained by substituting 15% by weight of the sugar of the basic mix, with the starch sugar composition has color, taste, luster and melting in mouth all better than the basic mix. Stated specifically, the former was evaluated to have a good color since it was colored with difficulty by heating because the starch sugar composition had a better heat resistance than the sugar, have preferably a mild taste, and have been improved to have a superior texture such as luster and melting in mouth.

As described above, according to the process of the present invention for producing the starch sugar composition, syrup containing the nigerooligosaccharide or a reduction product thereof in a content as high as at least 30% by weight in saccharide solid content can be mass-produced at a low cost. Hence, starch sugar compositions having various preferable properties, e.g., having a low sweetness of about 25 to 55% of that of sucrose, a superior heat resistance, low coloring properties and a moisture retention effect can be economically obtained. The starch sugar composition may be added to food and drink, whereby not only a sweetness can be imparted, but also the quality of sweetness can be improved, the moisture retention of foods can be improved, and various advantages such as lustering, prevention of denaturation of protein and body-providing can be provided. Hence, it can be used as a sweetener that can answer the high-level demand recently made on saccharides.

What is claimed is:

1. A process for producing a starch composition comprising:

contacting an aqueous saccharide solution with a solid content of at least 10% by weight and which contains a saccharide having a degree of glucose polymerization of 2 or more in an amount of at least 50% by weight of the total saccharide content with an enzyme produced by the organism Acremonium sp. S4G13 which produces nigerooligosaccharides by a transglycosylation reaction or a condensation reaction, or by both a transglycosylation and a condensation reaction, to form nigerooligosaccharides in a total amount of at least 30% by weight of the total saccharide solid content of the solution, wherein the nigerooligosaccharide forming enzyme is added to the aqueous saccharide solution in an amount of from 0.01 to 5 units per gram of saccharide and allowed to act on the saccharide in the solution under the conditions of pH from 4 to 10 and temperature from 30° C. to 70° C.

2. The process according to claim 1, wherein said aqueous saccharide solution provided is produced by a process comprising contacting a starch-liquefying solution which has a solid concentration of at least 10% by weight with at least one enzyme selected from the group consisting of an α-amylase, a β-amylase, an oligosaccharide-forming amylase and a debranching enzyme to form said starch-liquefying solution to obtain said aqueous saccharide solution.

3. A process for producing nigerooligosaccharides, comprising contacting a starch-liquefying solution having a solid concentration of at least 10% by weight with at least one enzyme selected from the group consisting of an α-amylase, a β-amylase, an oligosaccharide-forming amylase and a debranching enzyme, and with an enzyme produced by the organism Acremonium sp. S4G13 which enzyme produces nigerooligosaccharides by a transglycosylation reaction or a condensation reaction, or by both a transglycosylation reaction and a condensation reaction, wherein said simultaneous contacting results in the formation of nigerooligosaccharides in an amount of at least 30% by weight of the total saccharide solid content, wherein the nigerooligosaccharide forming enzyme is added to the aqueous saccharide solution in an amount of from 0.01 to 5 units per gram of saccharide and allowed to act on the saccharide in the solution under the conditions of pH from 4 to 10 and temperature from 30° C. to 70° C.

4. A process for producing nigerooligosaccharides, comprising:

contacting an aqueous solution which has a solid concentration of at least 10% by weight and which contains at least one member selected from the group consisting of a starch, a maltooligosaccharide with a degree of polymerization not lower than maltose, and a dextrin, with at least one enzyme selected from the group consisting of an α-amylase, a β-amylase, and a debranching enzyme, to obtain a resulting product;

contacting said resulting product with an enzyme produced by the organism Acremonium sp. S4G13 which produces nigerooligosaccharides by a transglycosylation reaction or a condensation reaction, or by both a transglycosylation reaction and a condensation reaction, to form nigerooligosaccharides, wherein the nigerooligosaccharide forming enzyme is added to the aqueous saccharide solution in an amount of from 0.01 to 5 units per gram of saccharide and allowed to act on the saccharide in the solution under the conditions of pH from 4 to 10 and temperature from 30° C. to 70° C.

5. A process for producing nigerooligosaccharides, comprising:

contacting a material comprised of at least one member selected from the group consisting of a starch, a maltooligosaccharide with a degree of polymerization not lower than maltose, and a dextrin, with at least one enzyme selected from the group consisting of an α-amylase, a β-amylase, and a debranching enzyme, and by an enzyme produced by the organism Acremonium sp. S4G13 which produces nigerooligosaccharides by a transglycosylation reaction or a condensation reaction, or by both a transglycosylation reaction and a condensation reaction, to form nigerooligosaccharides, wherein the nigerooligosaccharide forming enzyme is added to the aqueous saccharide solution in an amount of from 0.01 to 5 units per gram of saccharide and allowed to act on the saccharide in the solution under the conditions of pH from 4 to 10 and temperature from 30° C. to 70° C.

6. A process for producing a starch sugar composition, comprising reducing the nigerooligosaccharides obtained by the process according to claim 4.

7. A process for producing a starch sugar composition, comprising reducing the nigerooligosaccharides obtained by the process according to claim 5.

* * * * *